(12) United States Patent
Zhang et al.

(10) Patent No.: US 11,968,933 B2
(45) Date of Patent: *Apr. 30, 2024

(54) TREE OR PLANT PROTECTION MAT

(71) Applicant: ZYNNOVATION LLC, Ashland, VA (US)

(72) Inventors: Wei Zhang, Midlothian, VA (US); Hailing Yang, Midlothian, VA (US)

(73) Assignee: ZYNNOVATION LLC, Ashland, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/819,726

(22) Filed: Mar. 16, 2020

(65) Prior Publication Data

US 2021/0161084 A1    Jun. 3, 2021

Related U.S. Application Data

(63) Continuation of application No. 16/218,030, filed on Dec. 12, 2018, now Pat. No. 10,624,276, which is a
(Continued)

(51) Int. Cl.
*A01G 13/02* (2006.01)
*A01G 9/033* (2018.01)
(Continued)

(52) U.S. Cl.
CPC .............. *A01G 24/35* (2018.02); *A01G 9/033* (2018.02); *A01G 13/0268* (2013.01); *A01G 13/0281* (2013.01); *A61L 11/00* (2013.01); *B29B 17/02* (2013.01); *C05D 1/005* (2013.01); *C05F 3/04* (2013.01); *C05G 3/00* (2013.01); *C05G 5/16* (2020.02); *C08J 11/04* (2013.01); *B29B 2017/0203* (2013.01); *B29B 2017/0244* (2013.01); *B29L 2031/4878* (2013.01); *C08J 2300/14* (2013.01); *E04D 11/002* (2013.01); *Y02A 30/254* (2018.01); *Y02A 40/20* (2018.01); *Y02B 80/32* (2013.01); *Y02P 20/143* (2015.11);
(Continued)

(58) Field of Classification Search
CPC ................ A01G 13/02; A01G 13/0268; A01G 13/0275; A01G 13/0281; A61F 2013/51443
USPC .................................................. 47/32, 32.8, 9
See application file for complete search history.

(56) References Cited

U.S. PATENT DOCUMENTS 4,622,036 A * 11/1986 Goodrum ........... A01G 13/0268
428/314.2
5,928,209 A * 7/1999 Bodford ............ A61F 13/51478
604/370
(Continued)

*Primary Examiner* — Peter M Poon
*Assistant Examiner* — Danielle A Clerkley
(74) *Attorney, Agent, or Firm* — Law Office of John K. Pike, PLLC

(57) ABSTRACT

One embodiment provides a modular green roof tray, house plant growth media and horticulture growth media, and a tree protection mat for weed and moisture control made from recycled disposable diapers. The growth medium and tree protection mat contain superabsorbent materials from diaper that can absorb waters and greatly reduce irrigation so to provide a drought resistant feature. One embodiment also provides a manufacturing process to perform 100% recycling of disposed diapers.

9 Claims, 15 Drawing Sheets

Top View

Related U.S. Application Data continuation of application No. 15/401,733, filed on Jan. 9, 2017, now Pat. No. 10,178,834, which is a continuation of application No. 14/346,964, filed as application No. PCT/US2012/056967 on Sep. 24, 2012, now Pat. No. 9,565,809.

(60) Provisional application No. 61/538,565, filed on Sep. 23, 2011.

(51) Int. Cl.
*A01G 24/35* (2018.01)
*A61L 11/00* (2006.01)
*B29B 17/02* (2006.01)
*C05D 1/00* (2006.01)
*C05F 3/04* (2006.01)
*C05G 3/00* (2020.01)
*C05G 5/16* (2020.01)
*C08J 11/04* (2006.01)
*B29L 31/48* (2006.01)
*E04D 11/00* (2006.01)

(52) U.S. Cl.
CPC .............. *Y02P 20/145* (2015.11); *Y02W 30/52* (2015.05); *Y02W 30/62* (2015.05)

(56) References Cited

U.S. PATENT DOCUMENTS

| | | | |
|---|---|---|---|
| 6,195,935 B1* | 3/2001 | Bellucci | A01G 13/0281 47/9 |
| 2005/0047868 A1* | 3/2005 | Byles | A01G 25/00 47/20.1 |
| 2005/0178056 A1* | 8/2005 | Morrone | A01G 13/0268 47/9 |
| 2009/0133325 A1* | 5/2009 | Kraminer | A01G 13/02 47/31.1 |

* cited by examiner

TREE OR PLANT PROTECTION MAT

All or part of the subject matter described herein was carried out under NSF-SBIR Award 1046780. The government may have rights in the subject matter described herein.

BACKGROUND

Green roof systems are used on the roofs of buildings and provide an environment to host vegetation. A green roof system can offer energy consumption reduction, sound insulation, food and flower production, reduction of greenhouse gas emission, preservation of habitat and biodiversity, storm water retention, reduction in the urban heat island effect, and other benefits.

The main concerns for a green roof system include structural strength, managing or avoiding water leakage, and irrigation of roof plants. A building with a green roof must be strong enough to support the growth medium and the plants, especially after it is saturated with water. Waterproofing is a challenge as there may be a sustained water pressure on the roof in some systems. The aforementioned aspects are important for an intensive green roof, while irrigation is important for an extensive green roof. Current green roof technologies uses light weight growth medium to reduce the load on the infrastructure. For flat roofs, the main concerns are waterproof and structural design. For inclined roofs, the growth medium immobilization and water retention need extra considerations. Pitched sheets or stair-like designs have been used for this type of roof. The thinner growth medium layer of an extensive green roof allows less water uptake and retention. In areas with infrequent precipitation and/or high evaporation rates, irrigation may be required on a daily basis, which may offset the cost savings from a green roof system.

A similar situation requiring an environment to host vegetation exists in tree protection. Tree protection is important, especially for young and newly planted trees, whose root system has not yet well developed. Most widely used method is mulching with wood chips that are recycled from green waste. This can preserve moisture, reduce competition from weeds, and allow trees obtain essential nutrients to survive early growth. But they are not very efficient and long-lasting and will degrade quickly. Usually trees need to be re-mulched annually in spring.

One alternative solution for tree protection, especially for young trees, is to place weed mat around tree. These weed mats are usually made of plastic materials whose functions are just like mulch but last longer. Two different types of mats are available on the market right now: mats with and without pores. The major difference is that weed mat with pores allows rain water seep in while weed mat without pores cannot. It seems weed mat with pores are more effective for water permeate through; however, it is less favorable for the customers in the market. The argument preferring mat without pores is that the same pores that allow water seep in can quickly evaporate out because of its high surface area and small pore sizes. Both types of weed mats and wood chips' mulches rely primarily on the soil around trees for holding moisture. The mat or the mulch has no or very limited capability to absorb water. Therefore the moisture content can vary in a wide range depends on the properties of soil and weather.

Meanwhile, hundreds of billions of dirty diapers are disposed annually as solid wastes and only a very small fraction of them are recycled. This is mainly due to the lack of technologies for efficient and cost-effective recycling. The valuable materials in these disposed diapers could have found great applications if they can be properly processed.

Disposable diapers are made of a variety of components. First, an absorbent pad made of cellulose or cellulose acetate and superabsorbent polymer (SAP) e.g., sodium polyacrylate is used to absorb body fluids. This pad is then placed into a tissue carrier, which can be made of polyester nonwoven fabrics or tissue paper. This tissue wrapped pad is then sandwiched in between a layer of nonwoven fabric for interior and a non-permeable film for exterior. The nonwoven fabric includes of a hydrophilic layer to allow water to flow to the absorbent pad and a hydrophobic layer to keep the surface in contact with skin dry. The non-permeable film is made of polyethylene or cloth-like polyolefin films to prevent liquid leakage. To put all the above components together, hot-melt adhesives are used. Elastomeric materials, such polyurethane, polyester or rubber are used in cuffs for both the waist and the leg to maintain tightness. Adhesive tapes or hook tapes are used to provide mechanical grip for closure. Other components, such as lotions applied on the surface of top sheet, decorative film, wetness indicator, and acquisition and distribution layers are very common in disposable diapers.

The complexity of the disposable diapers arises from the consumers' need for a comfortable, effective, easy-to-use, and low-cost product. However, such a system has made traditional recycling impossible to do efficiently and cost-effectively with current technologies. As a result, most after-consumer disposable diapers end up as solid waste piling up in landfill fields. The lack of a product that can consume the recycled materials and proper purification technologies to produce high purity materials have played a great role in the landfill problem.

DETAILED DESCRIPTION OF THE SEVERAL EMBODIMENTS

Figure 1:
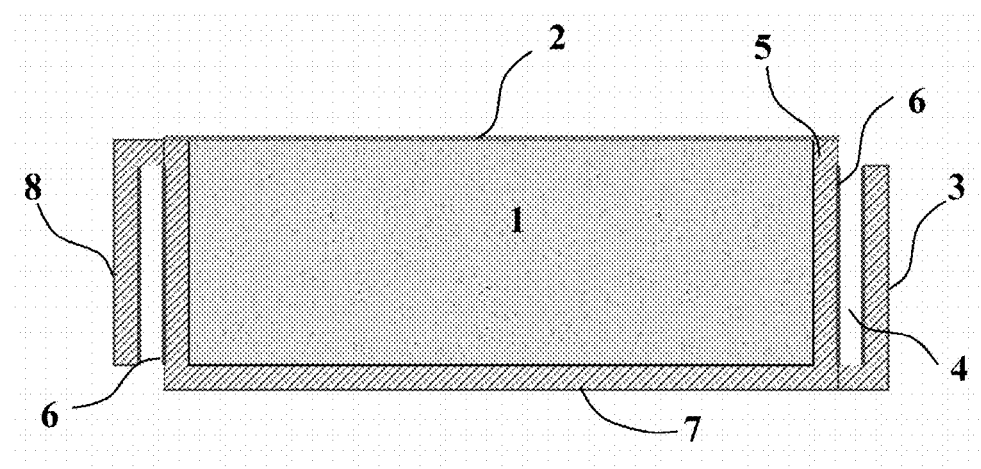
FIG. 1. Cross-section view of one embodiment of the modular green roof tray with snap-fit interlocking design. The components are 1, growth media; 2, cover; 3, tongue; 4, groove; 5, wall; 6, adhesive; 7, bottom layer; and 8, tongue.

One embodiment provides a light-weight, modular green roof tray with three layer structure. The bottom layer (waterproof layer) of which is made from recovered thermoplastic materials from recycling disposable diapers, the center layer of which is a drought resistant growth medium containing superabsorbent polymers, and the top layer of which is a porous nonwoven cover. This design also depicts a novel three-dimensional snap-fit locking mechanism. FIG. 1 illustrates this green roof module design.

One embodiment provides a modular green roof tray with a three-dimensional snap-fit locking mechanism. This snap-fit interlocking mechanism can be combined with adhesives so that they can be permanently connected to each other if such is desired. This design of snap-fit interlocking mechanism is superior to conventional systems in which 2-dimensional interlocking is used.

One embodiment provides a modular green roof tray with a cover using low density and large pore-sized nonwoven mat. This cover performs as an enclosure of growth medium during the shipping and installation, allows plants to grow through the pores, prolongs water retention time of growth medium, and prevents erosion.

One embodiment provides a modular green roof tray with a cover using low density and large pore-sized nonwoven mat. The water retention time with this non-woven mat is 70% longer than that without the mat.

One embodiment provides a composition for drought resistant growth medium in which the recovered and reinforced superabsorbent polymers (SAPs) from recycled disposable diapers is evenly mixed with soil that can be regular soil, peat moss, clay, expanded clay (commercial name as Perlite), or a mixture of them. SAP refers to the water absorbent materials recovered from diapers that include superabsorbent polymer particles and cellulose fibers. The composition range of recovered and reinforced SAPs can be in between 10-90% of the total wet weight of the growth medium, which range includes all values and subranges therebetween, including 10, 15, 20, 25, 30, 35, 40, 45, 50, 55, 60, 65, 70, 75, 80, 85, and 90% by weight, based on the total wet weight of the growth medium. In one embodiment, the composition is in between 40-75% of wet SAP weight.

One embodiment provides a composition for drought resistant growth medium that the saturated growth media contained 20% more water content but 20% weight lighter compared other commercially growth media for green roof at a certain depth. Due to the drought resistant and lightweight feature of this new growth media, architecture design, vegetation selection and maintenance will be much more flexible. Such growth media can be widely applied to different kinds of green roof: extensive, semi-intensive and intensive. It can provide more flexibility to design a green roof for architectures to meet the load capacity requirement. This kind of growth media is also applicable for non-modular green roof design. Such growth media can be used for the growth of various plants (grass, sedum, flowering and tall plants). It can also be used for indoor house plants and other horticulture plants. Our growth media has been proven to be applicable for extreme conditions such as drought, high temperature, low temperature and high precipitation.

One embodiment provides a young tree protection mat for weed control and moisture conservation with three layers structure. The bottom layer (semi-permeable layer) is a porous nonwoven cover to hold the center layer in place; the center layer is a water absorbing pad containing superabsorbent polymers; and the top layer is a nonpermeable or semipermeable panel or film made from recovered thermoplastic materials from recycling disposable diapers or any other plastic materials. The top layer has funnel shaped dips with holes that allow collection absorption of rain water by the absorption pad.

One embodiment provides a recycling procedure to separate, recover and reinforce superabsorbent polymers from recycled disposable diapers.

One embodiment provides a recycling procedure to recover thermoplastic materials from disposable diapers. These thermoplastic materials include polyolefins such as polyethylene and polypropylene, polyesters, and elastomers, etc.

One embodiment also provides a compounding procedure may be necessary to create high strength materials from the recycled thermoplastics and small quantity of cellulose materials due to insufficient separation.

One embodiment provides a new type of green roof module with novel drought-resistant and lightweight growth medium developed from recycled super absorbent polymers from disposable diapers. In addition to the benefits of regular green roof systems, this system offers a twenty percent increase in the amount of water absorbed and a twenty percent decrease in total weight for a given depth of growth medium. This will provide a much larger selection of plants and lower requirement for infrastructure. While it allows more existing buildings suitable for green roof installation, it means lower building cost for new constructions. In drought prone areas, the growth medium consumes less water at much lower frequency of watering. The presence of super absorbent polymers in the growth medium may also have superior stormwater management qualities due to water retention capability. The growth medium can also help contribute towards Leadership in Energy & Environmental Design (LEED) certification in the materials & resources category, especially the recycled content, regional materials, and rapidly renewable materials subcategories. Ordinary growth media used in the current green roof market do not necessarily qualify for these categories. The product can be a growth media alone or modular green roof products. In addition, the recycled super absorbent polymers can be used as a growth medium additive.

Other applications involving growth media are contemplated and considered within the scope. For example, it can be used as indoor and outdoor potting soil, greenhouse and nursery soils, and additives for general gardening. Entry into the modular greenroofing market lends itself easily to window garden modules, living walls and other potted edible plants for people with limited space and no garden access as well.

Soiled baby diapers collected in diaper bags are first sanitized using sodium hypochlorite solution (bleach) and cleaning. Baby feces and other human waste are separated from the diapers during this process. After initial cleaning and sanitation, diapers, plastic bags and wipes are then shredded allowed to settle down in water. Salts of different type are added to adjust the separation power of water. Due to their differences in density compared to water, these materials settle down as two layers. The top layer, which has lower density than water, is mainly thermoplastics, such as polyolefins (polyethylene or polypropylene fibers or strips), polyester nonwoven mats, elastomers etc. The bottom layer, which is heavier than water, is mainly soaked SAP and cellulose fibers and partially polyesters. The separation efficiency by this method is very limited. Therefore the purity of each separated portion is too low for other uses of them. Advantageously, the application does not require high purity materials. A small fraction of virgin plastic resins or other higher purity recycled materials may be used to improve the waterproof performance if required.

After this partial separation of different diaper components, the polyolefin portion will be compression-molded into square pans at high temperatures (above the melting temperatures of polyolefins) as shown in FIG. 1. These pans are to hold growth medium, provide a waterproof or water permeable bottom layer (7) and 4 side walls (5) and support the weight of the whole module. During the compression molding, snap-fit interlocking structures are incorporated. Two tongues (3 and 8) and grooves (4) of the snap fit interlocking structure are molded on to each pan. Adhesives (6) can be applied inside the groove to permanently connect adjacent trays together.

Figure 5:
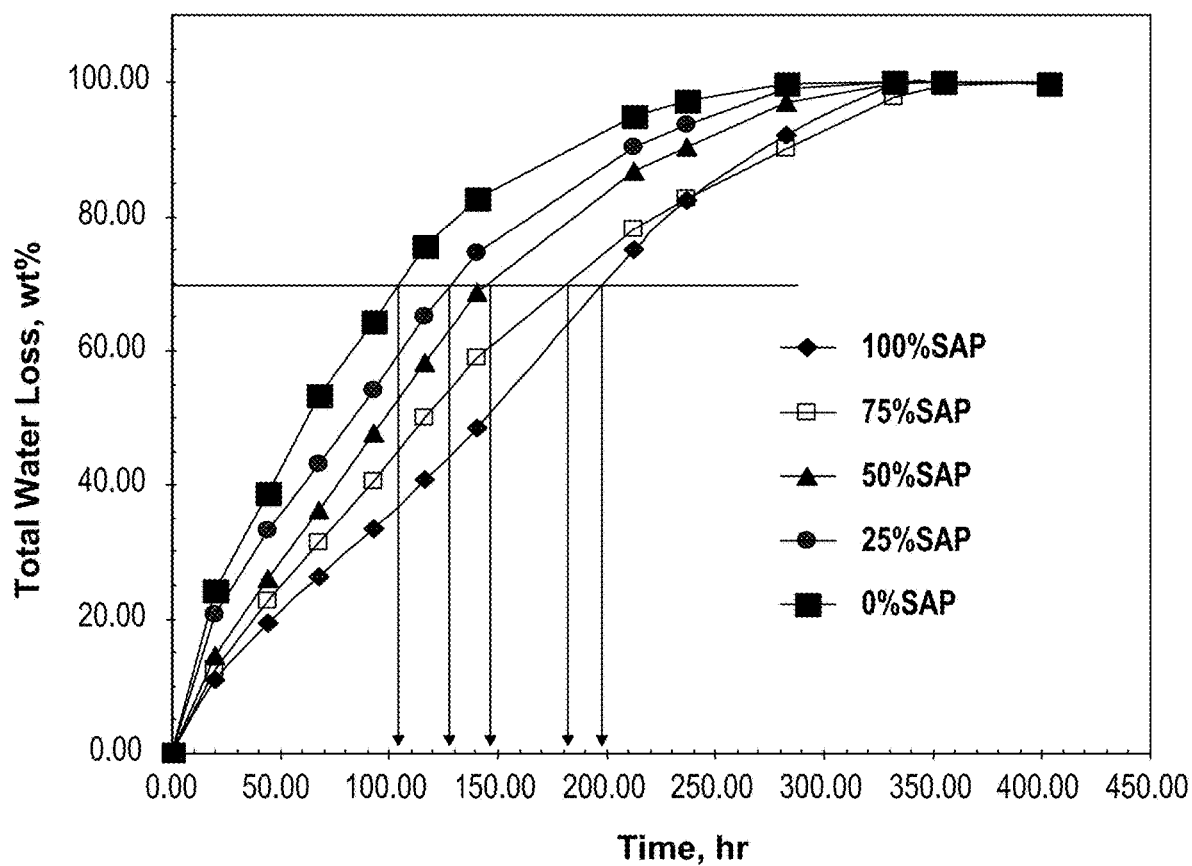
FIG. 5. Graphically presents the effects of SAP on the water loss without nonwoven cover. The effects of SAP content on the water loss of growth media without nonwoven cover. All the growth media were soaked for at least 2 hours before free flowing water was removed. Then the containers for growth media was kept under constant artificial sun light exposure till their weight is not changing over a period of 48 hours.
Figure 6:
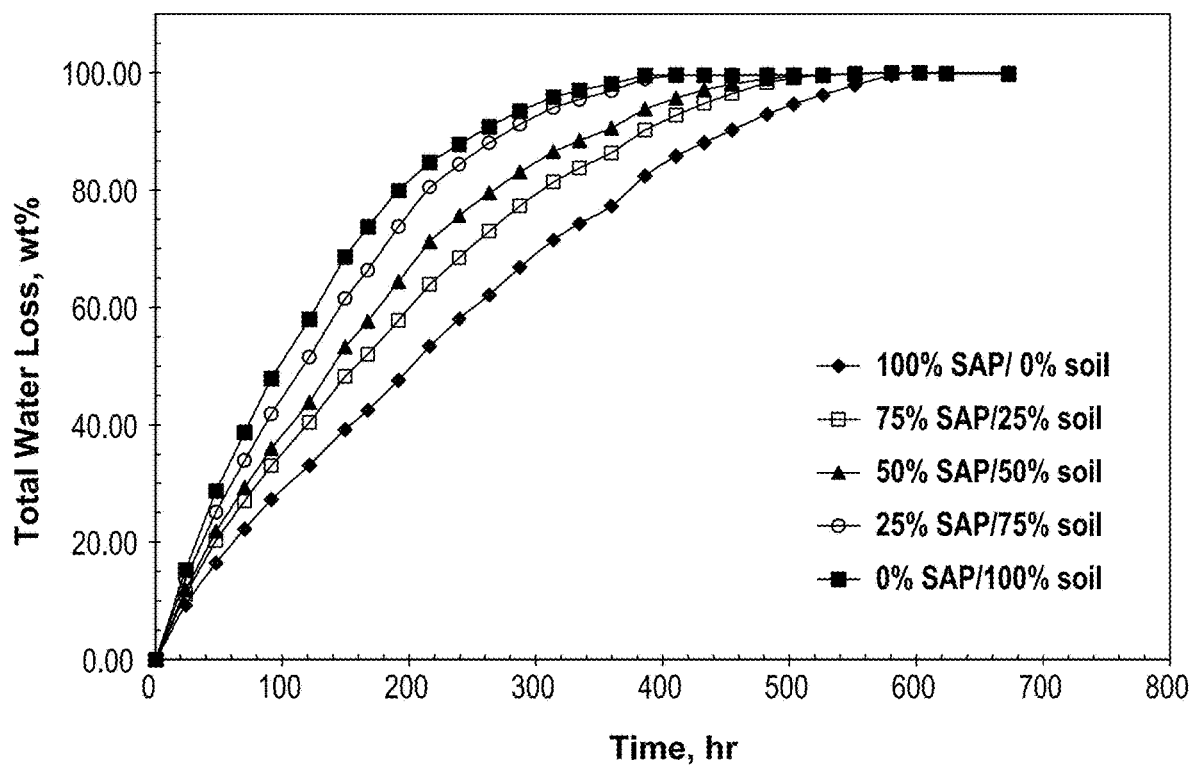
FIG. 6. Graphically presents the effects of SAP on the water loss with nonwoven cover. The effects of SAP content on the water loss of growth media with nonwoven cover. Growth media were soaked, and free water were removed before the nonwoven covers were added. The containers for these growth media was exposed to the same conditions as those without nonwoven covers and weighted ever 24 hour till their weight stable over a period of 48 hours.

After the pans are manufactured, growth medium (1) are placed inside the pan. Growth medium can be in wet state, as one component of the growth, recovered SAP are in wet state. The growth medium includes recovered SAP and light weight soil. Lightweight soil is made of 22.74 vol % expanded clay (Miracle-Gro® prelate), 68.22 vol % peat moss (Miracle-Gro® peat moss) and 9.04 vol % water. Other light weight soils may be used. FIGS. 5 and 6 show the relationship between the composition of growth medium and the water retention with or without nonwoven covers (2). Degree of water loss decreases with the increase of SAP content. The 30% water retention time is almost double with SAP content range from 0% to 100%. Therefore, their drought resistance performance can be dramatically different. To test their drought resistant performances, 400 Penkoted® grass seeds or 25 transplanted grasses were planted in the above growth media in containers of 20 cm×20 cm×4.5 cm dimensions. After one month with little irrigation, only the grass in the containers with 75% SAP/25% soil and 50% SAP/50% soil in volume was observed alive. Fine tuning tests have been carried out by applying 400 Penkoted grass seeds into the same size container in order to determine the optimum content of out growth medium. The results indicated 65% SAP/35% soil is the optimum content of our growth medium. Examples 1 and 2 illustrate the growth medium performance.

Woven or nonwoven fabrics that can be polyester, polypropylene or nylon are welded onto the top of pans. The nonwoven or woven fabrics are specially chosen so that their pores are large enough for plants, such as grass grows through. The water retention time by using nonwoven/woven fabrics cover can be up to 70% longer and more than those without such kind of cover. This range includes all values and subranges therebetween, including up to 10, 20, 30, 40, 50, 60, and 70% and longer.

In the case that water is present in the shredded mixture of thermoplastics and superabsorbent polymer particles, the first salt solution may be obtained by adding solid salt to the shredded mixture, optionally with stirring. Water may be leftover in the shredded mixture from the sanitizing step, it may be added after the sanitizing step, or it may be leftover after rinsing the sanitized diaper components, or it may be added after a rinsing step, or any combination of two or more thereof. Alternatively, the first salt solution may be first prepared from water and the salt, and then this solution is contacted with the shredded mixture. Alternatively, the first salt solution may be obtained with a combination of addition of sold salt to the shredded mixture and addition of salt solution to the shredded mixture. In one embodiment, the salt or salt solution is contacted with the shredded mixture and is accompanied by stirring or agitation or both.

In one embodiment, an amount of solid salt is added to the shredded mixture to form the first salt solution and effect separation of the upper and lower layers. In one embodiment, a sufficient amount of salt solution is added to the shredded mixture to form the first salt solution and effect separation of the upper and lower layers. In one embodiment, the salt solution is the first salt solution. In another embodiment, the first salt solution is formed at the time of adding salt or salt solution to the shredded mixture. In one embodiment, the concentration of the salt solution is not particularly limited, and may suitably range from greater than 1 to 70% by weight. This range includes all values and subranges therebetween, including greater than 1, 2, 3, 4, 5, 6, 7, 8, 10, 15, 20, 25, 30, 35, 40, 45, 50, 55, 60, 65, and 70% salt by weight, based on the total weight of salt solution. In one embodiment, the concentration of the first salt solution is not particularly limited, and may suitably range from greater than 1 to 70% by weight. This range includes all values and subranges therebetween, including greater than 1, 2, 3, 4, 5, 6, 7, 8, 10, 15, 20, 25, 30, 35, 40, 45, 50, 55, 60, 65, and 70% salt by weight, based on the total weight of first salt solution. In one embodiment, the concentration of the salt solution or first salt solution is about 10% by weight based on the total weight of the solution.

During the separation of diaper components, a certain water solutions of sodium chloride, potassium chloride, sodium carbonate, potassium carbonate, calcium chloride, calcium sulfate, or mixture of two or more of them are added into the separation medium to adjust the separation power. The separation power of water is adjusted by addition of inorganic salts in that salts will reduce the water uptake of SAP particles. If salts are not added, SAP particles are swelled at their maximum, which lowers their density resulting in poor separation. Water soluble calcium solutions are added to adjust the gel strength of SAP by forming calcium polyacrylate outside of the SAP particles (Scheme 1). Calcium polyacrylate is not a superabsorbent polymer; therefore it behaves as a physical crosslinker when they occur in or outside of the SAP particles. The ratio of water soluble calcium (in the equivalent to calcium chloride) to dry SAP should be maintained at lower than 3:10 by mass. Higher calcium amount can crash SAP particles and produce a non-superabsorbent polymer, which was used as a process to remove SAP from the desired pulp products in the diaper recycling pilot plant by Procter & Gamble and the Seattle Solid Waste Utility and Rabanco Recycling Company in Seattle WA. In one embodiment, the crashed SAP may be subjected to a further recovery procedure to replace calcium cations with either sodium or potassium. Examples 3 and 4 provide procedures and recipes for separation of diaper components as well as SAP recovery using dilute sodium or potassium chloride solution as separation medium. Example 5 provides a procedure and recipe for separation of diaper components as well as SAP recovery and reinforcement using dilute calcium chloride solution as separation medium. Example 6 describes how to recover calcium crashed SAP using a water soluble carbonate salt.

Scheme 1. SAP reinforcement using calcium chloride

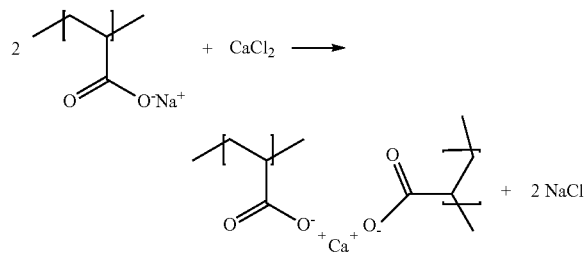

Higher calcium concentration in the separation medium or in subsequent treatments may be desirable only when SAP is very hard to separate from the rest of the materials. The complexity of the materials used in a diaper, together with the number of different manufacturers and brands, can lead to situations where two or more different materials are welded together and their densities are in the similar range of swelled SAP particles. A calcium concentration at which calcium to SAP weight ratio is 1:1 can reduce the swell ratio of SAP to less than 3 times of SAP's own weight. Sodium or potassium carbonate can be used to recover calcium crashed SAPs. The reaction is shown in Scheme 2. Example 5 and 6 provide a procedure and two recipes for SAP recovery after crashed by high calcium solutions.

Scheme 2. SAP recovery reaction using sodium or potassium carbonate

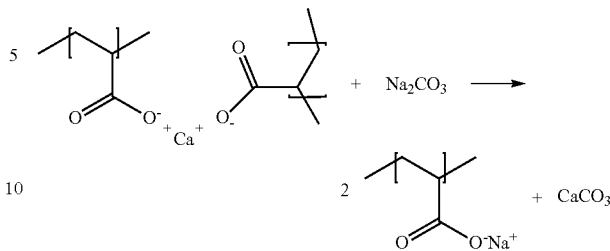

Thermoplastic polymers are made up a big fraction of materials in a disposable diaper. These materials include polyethylene, polypropylene, and elastomer. All of these materials has a specific gravity less than 1, which allows them float in water separation medium. A simple wet separation process can produce thermoplastics and SAP particles. A wetlay process (U.S. Pat. No. 5,409,573) that is similar to paper making process can be used to lay each of the component onto a conveyer belt and dry separately for later molding process. SAP can also be maintained in wet state till the last step of green roof module assembling procedure.

Due to the mixture nature of the recovered thermoplastics, which contains polyethylenes, polypropylenes, polyesters, polyacrylics, elastomers and cellulose fibers, direct molding of this mixture would lead to modules with poor mechanical properties. A compounding process using twin-screw extrusion method can mix these components up to produce a polymer blend with much improved mechanical properties. Example 7 and 8 discusses these two situations where the strength and elongation at break of the compressed sheet are dramatically different.

One embodiment relates to using recycled diaper materials to produce a super drought resistant and lightweight green roof module product. The inventors have found similarities in green roof materials and disposable diapers. The different components disposable diapers have been separated with simple, economical and environmentally benign manufacturing and processing. The separated materials were used to form different parts of green roof modules. The thermoplastic materials in a disposable diaper may be reprocessed into the green roof tray, while the super absorbent particles may be combined with other growth media into novel high water retention growth media. The high water absorbance feature of disposable diapers is converted into the drought resistant feature of green roof products. The lower densities of thermoplastics and super absorbent materials compared to gravel and regular soil is transformed into the lightweight feature of the proposed green roof module.

One key procedure during this recycling process is the separation of different diaper components. Based on their relative densities in water, the components in a diaper can be roughly separated into two categories: those float (polyolefins) and those sink (superabsorbent, pulp and small quantity of polyester nonwoven). The inventors have found that wetlay technology, such as used in paper-making processes may be used for both the separation and the consequent mat formation using water with or without other additives as the separation medium. Both the proposed product (high tolerance to material purity) and the recycling and processing procedures preclude the strict requirements of traditional lengthy and costly recycling processes, for which high purity components are the target product.

One embodiment provides a growth medium containing superabsorbent materials, which can absorb much more water than commercially available growth media. The water uptaking ability can greatly reduce irrigation so to provide a drought resistant feature. Given a certain growth medium depth, the growth media may contain 20% more water while its total weight can be reduced by 20% comparing current products on the market. The present study also shows the feasibility to perform 100% recycling of disposed diapers using the proposed economical recycling and manufacturing processes.

Figure 2:
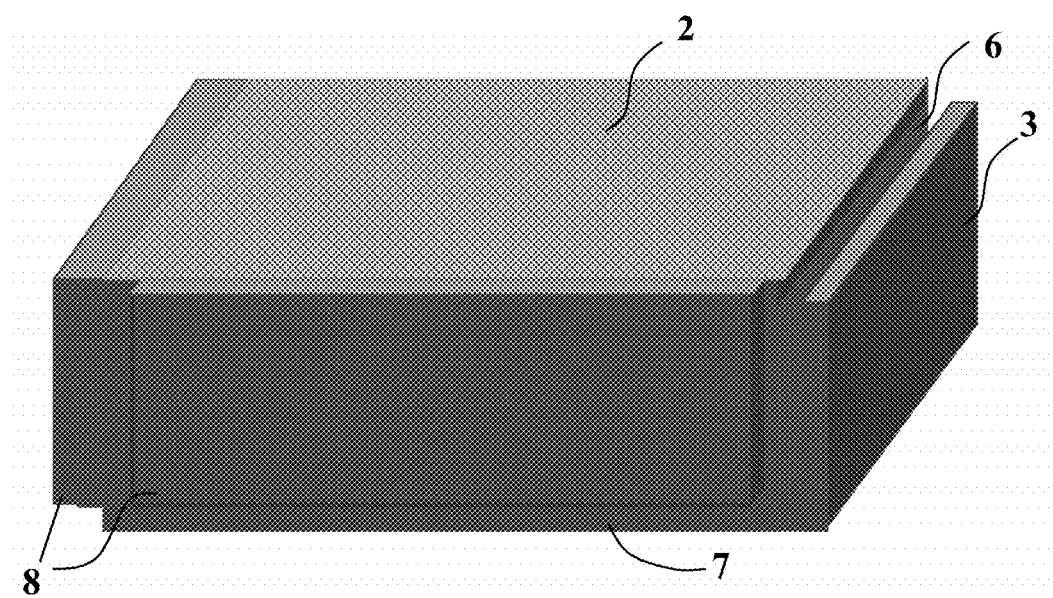
FIG. 2. Whole view of one embodiment of the modular green roof tray with snap-fit interlocking design.

It has now been found that the rate of relative water loss decreases with the increase of content of superabsorbent polymers. The water retention time (at 70% water loss) is almost double with SAP content range from 0% to 100% as shown in FIG. 2. In this test, SAP refers to the water absorbent materials recovered from diapers that include superabsorbent polymer particles and cellulose fibers.

Figure 3:
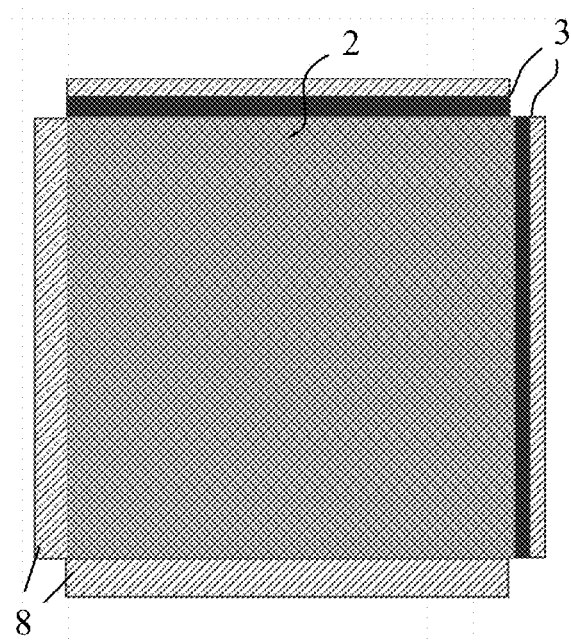
FIG. 3. Top view of one embodiment of the modular green roof tray with snap-fit interlocking design.
Figure 4:
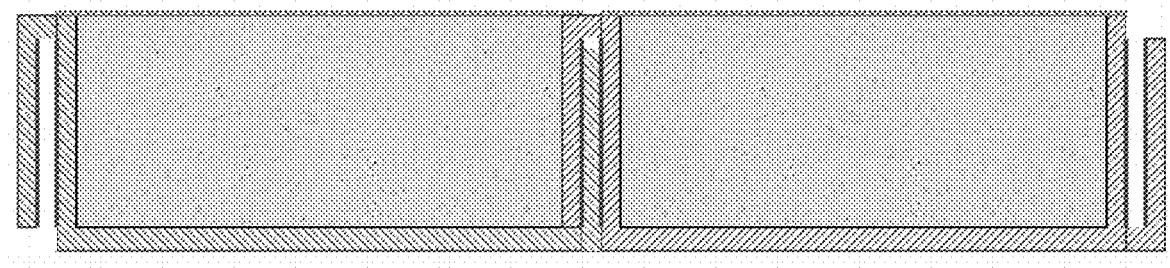
FIG. 4. Two modular green roof trays connected together using one embodiment of snap-fit interlocking design.

The use of nonwoven cover provides an enclosure of growth medium during the shipping and installation. It also allows plants to grow through the pores, prolongs water retention time of growth medium, and prevents erosion. The results also indicate that the water retention time with this non-woven mat is 70% longer than that without the mat, as shown in FIG. 3.

Figure 8:
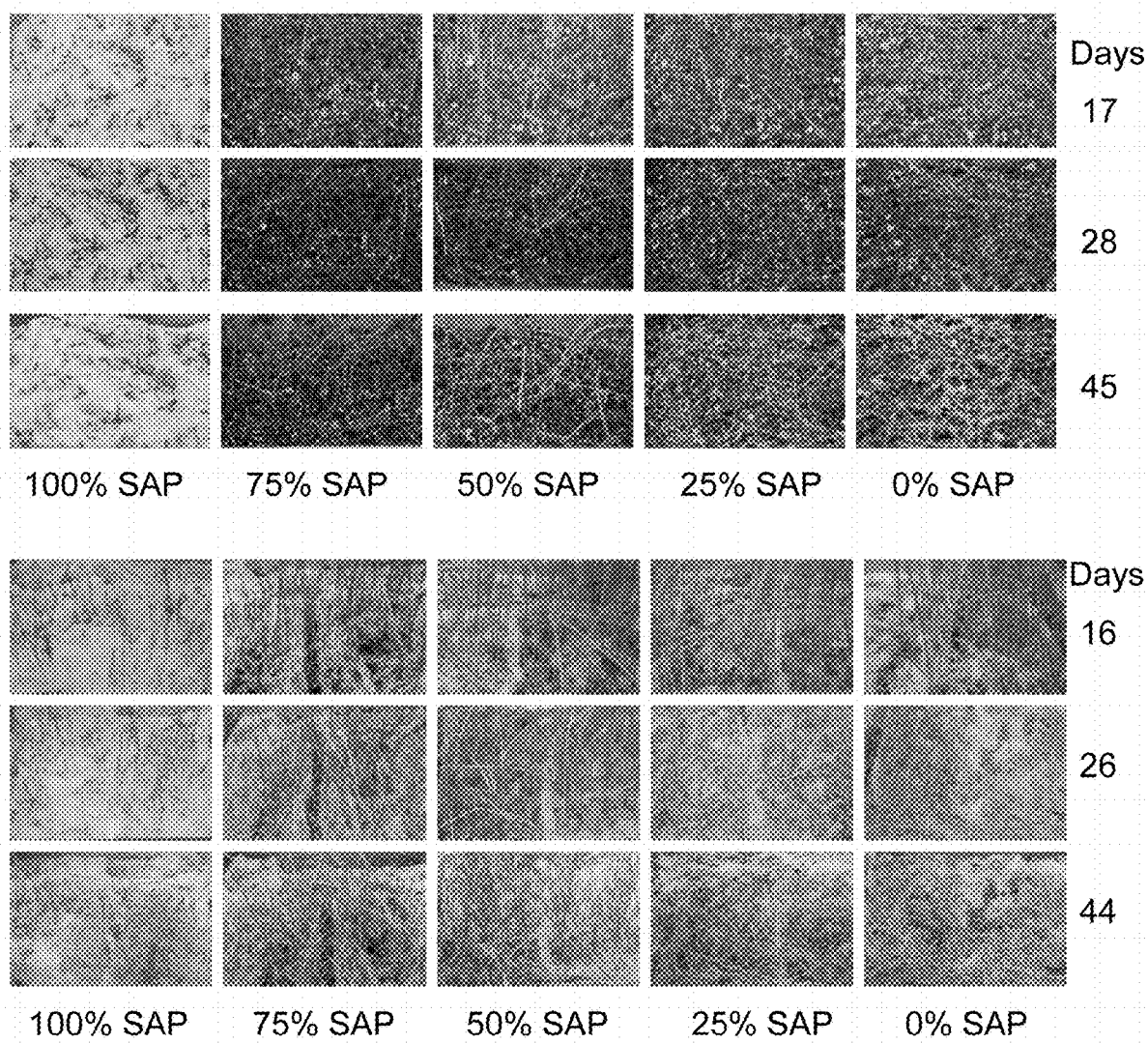
FIG. 8. Exhibit of vegetation establishment from seeds in growth media without nonwoven cover (upper set of images) and with nonwoven cover (lower set of images). For the group without nonwoven cover, the grass was sprouting and growing much less in the container with 100% SAP because of poor air permeability and poor root development. The sparsely sprouted grasses in this container died after two weeks. The grasses in the containers with 25% and 0% SAP initially sprout similarly with other two containers with 75% and 50% SAP. However, the growth of grasses in the former two containers eventually became slow and died in four weeks. In contrast, the two containers with 75% and 50% SAP were able to keep the grasses alive till 45th day with regular watering. After that, the grasses survived another two weeks without watering. The total water consumption of each container is 3000 ml. For the group with nonwoven cover, the sprouting and growth was similar except the total water usage is only 1800 ml for each container. Moreover, nonwoven cover did not inhibit sprouting and growth.

In one embodiment, the growth medium compositions, considering growth and drought resistance, is about from 40-75% of wet SAP weight. The balancing components can be commercially available growth media. However, in one embodiment, iron containing soil may be avoided. FIG. 8 shows comparison of the vegetation establishment in different growth medium compositions with or without nonwoven covers.

The results also show that the saturated growth media contained 20% more water content but 20% weight lighter compared other commercially growth media for a given green roof growth media depth, which determines what and how plants grow. This feature, together with the drought resistant and lightweight features provide flexibility for architecture design, vegetation selection and maintenance.

One embodiment provides a recycling procedure to separate, recover and reinforce superabsorbent polymers (SAP) from recycled disposable diapers. Several inorganic salts can be added to the separation medium and this treatment reinforces SAP by making a physically crosslinked network in addition to the build-in chemical network in SAP particles (Schemes 1). This degree of the crosslinked network can be adjusted using a recovery reaction based on water absorbance design requirements (Scheme 2). The advantages of this procedure are (1) dramatically increasing the efficiency for separation of disposable diaper components; (2) retardation of SAP degradation in growth medium and avoiding the potential contamination to substantial environment.

Figure 9:
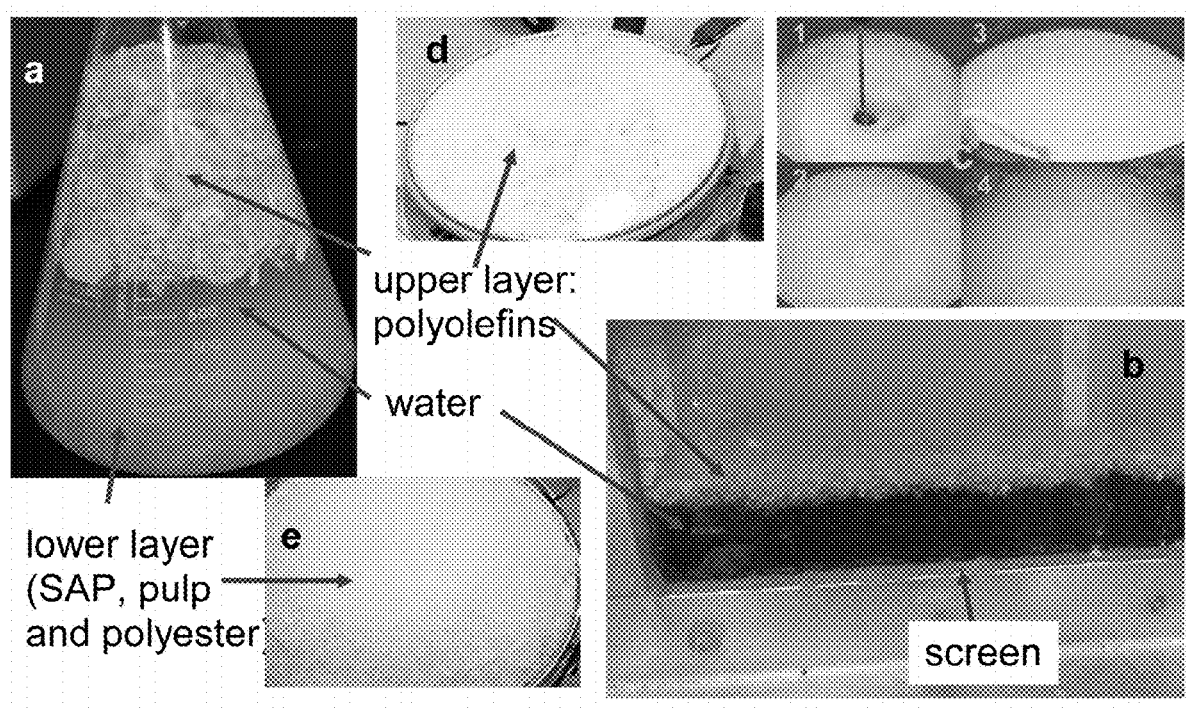
FIG. 9 Exhibit showing one embodiment of separation of diaper components. Pictures showing separation of diaper components using wet method, wetlay separation and mat formation processes. a, diaper components separated into two groups based on their densities: polyolefins float and SAP, pulp fibers and polyesters sink, b, mat formation by wetlay process at USDA FPL, c, wet separation process: c1, agitation for mixing, c2 and c3, components settle down after agitation stopped, c4, lower layer is shown after upper layer decanted, d, upper layer separation and drying, e, lower layer separation and drying.

In one embodiment, thermoplastic materials may be recovered from disposable diapers using wetlay process, a compounding procedure for homogenize the recovered materials, and a optionally compression molding procedure to make green roof trays or other engineering materials. FIG. 9 shows pictures taken during separation and wetlay processes indicating the separation of different diaper components in separation medium.

Figure 10:
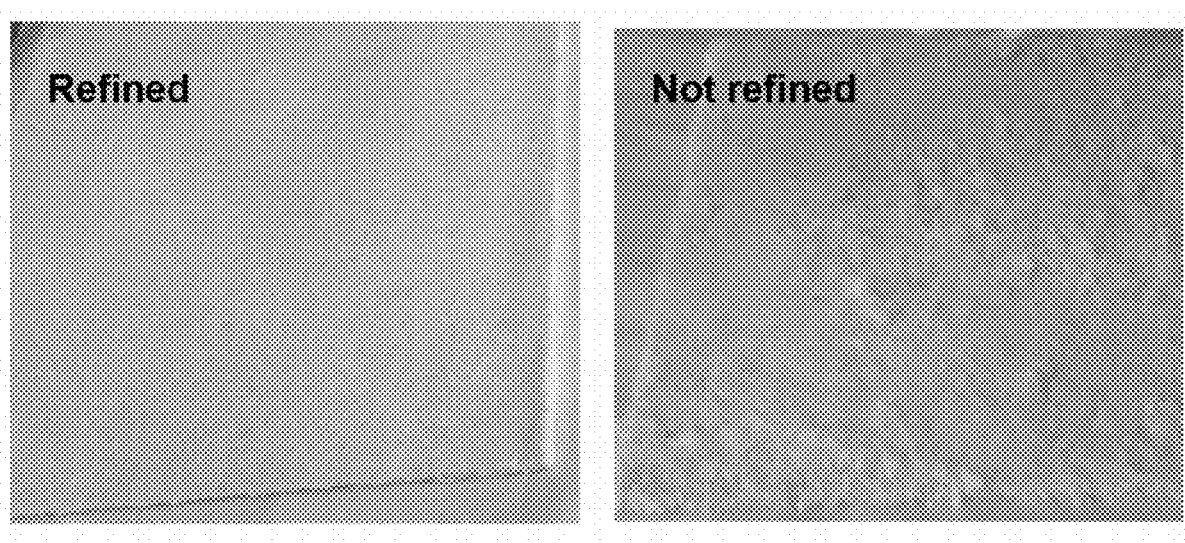
FIG. 10. One embodiment of nonwoven mats that were prepared by wetlay process with or without refining procedure FIG. 11. Graphically shows total organic carbon of water samples collected from water/SAP mixtures. Total organic carbon of water samples collected from water/SAP mixtures under heat (50° C.) and ultraviolet irradiation as well as the water sample collected after treatment. Tap water was used as a control and shown as Time=0 months.

In one embodiment, a refining process may be used in addition to the wetlay process. This refining procedure allows formation of a uniform, high strength, clean, and easy-handling mat. FIG. 10 shows a comparison of the nonwoven mat prepared with and without refining procedure.

Figure 11:
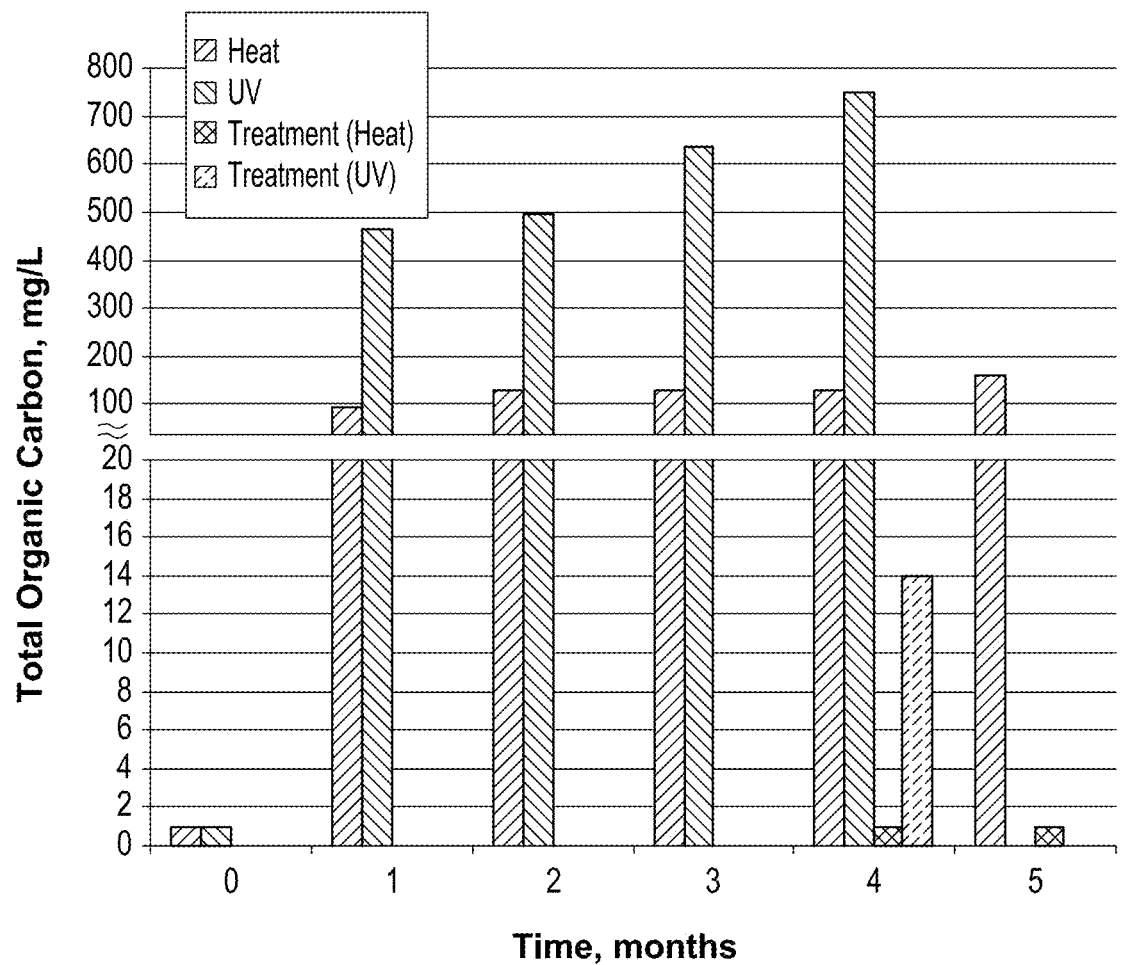

It has now been found that soluble SAP can cause high amount of total organic carbon (TOC) content in degradation tests. A treatment procedure was developed to lower TOC to undetectable level by using an economical precipitation agent. (FIG. 11)

One embodiment provides a procedure for cleaning and sanitation of dirty disposable diapers. Preliminary microbiology test has shown that bacteria can be completely killed following this process. Table 1 shows the microbiological test results.

TABLE 1

Microbiology Tests results

| Water Sample | Comments for Sample Collection | Bleach solution with 6% sodium hypochlorite, ml | Total Coliform, MPN/100 ml |
| --- | --- | --- | --- |
| Water with dirty diapers soaked in | 2 dirty diapers placed in trash can at ambient conditions for 1 week and then soaked into 20 L water | 0 | >2419.6 |
| Water after $1^{st}$ addition of bleach | Add 50 ml bleach solution, stir and wait 30 min before water sample collection. | 50 | 11.0 |
| Water after $2^{nd}$ addition of bleach | Add 50 ml more bleach, stir and wait 30 min before water sample collection. | 100 | 2 |
| Water after $3^{rd}$ addition of bleach | Add 50 ml more bleach, stir and wait 30 min before water sample collection. | 150 | <1 |

Pre-customer disposable diapers were ground by using wood chipper shredder, which was originally designed process. However the working mechanism of this type of machine is not suitable for handling soft materials like disposable diapers. The machine clogged very often and the shredded parts did not meet the requirement for an efficient separation in water. A commercial grade paper shredder machine, equipped with twin-shaft grinding gears was then used for this task. Although multiple passes have to be done to obtain small pellet sizes (~5 mm in linear dimension), the resulted shreds were acceptable for separation by wet method. A parallel attempt was also made to grind the diapers into finer particles by using a plastics grinder at Akron University. These fine particles (~1 mm in linear dimension), however, did not allow efficient separation in water or the other separation media. The reason for the separation dependence on particle size is unknown at this moment. But further study and optimization is required for better separation.

By using pure water as the separation medium, visual separation can be seen as shown in FIG. 9a. But the separation efficiency is very low because the SAP particles are highly swelled and occupying much of the volume in the vessel. The viscosity of water appeared to be high as well. Also due to the high swell ratio of SAP particles, their densities are essentially same as water. This problem is addressed by using salt solutions.

Only two layers of the three layers settlement were seen because polyester nonwoven cannot differentiate from SAP particles in density. The reasons are that polyester nonwoven has high porosity, in which SAP particles may present and they were treated for hydrophilicity also. But since polyester nonwoven are minor components, it was not further separated. Therefore the polyolefins and the rest can be separated very well, especially in salt solutions.

It is conventionally considered that disposable diapers contain 7% of polyester nonwoven fabric. However, it has now been found that this is only qualitatively correct for some brands of diapers. Therefore, in one embodiment, polyester nonwoven is not recovered as a separate component.

As mentioned above, the separation efficiency of pure water was very poor. In addition it took a long time and large quantity of water to separate very small amount of diaper components. To solve this problem, the swelled volume of SAP particles must be reduced, i.e., the density may be increased.

Aqueous solutions of sodium chloride, potassium chloride, sodium carbonate, potassium carbonate, calcium chloride, calcium sulfate, or mixture of two or more of them are added into the separation medium to adjust the separation power. The separation power of water is adjusted by addition of certain amount of inorganic salts in that salts will reduce the water uptake of SAP particles. If salts are not added, SAP particles are swelled at their maximum, which lowers their density resulting in poor separation. When water soluble calcium salts are added, a calcium polyacrylate salt is formed (Scheme 1), which is not a superabsorbent polymer and does not swell in water. This originally thought unsuitable reaction was used to form a chemically crosslinked network in the SAP particles. By controlling the percentage of this network, the gel strength as well as the water uptaking capacity of SAP particles can be adjusted. This reaction can also be used to sequester water soluble portion of SAP, which may otherwise increase total organic carbon content in the waste water stream and the runoff water from the green roofs.

In one embodiment, a wetlay process may be used for one or both separation and sequential mat formation. A wetlay trial run was successful. In one embodiment, a simple system with the most basic components of a wetlay process may be used to separate and clean materials. In carrying out or optimizing the process, one may consider solid/water ratio, salt concentration, agitation intensity, amount of reusable separation medium (salt water), overall water usage, and drying time for wetlaid mat. Non-limiting examples of wetlay processes may be found at U.S. Pat. No. 5,409,573, issued Apr. 25, 1995 and "Bamboo Fiber Reinforced Eco-Composites by Wetlay Processing" Zhang, Wei, et al., ANTEC 2007, pp. 2260-65, the relevant contents of each of which being hereby incorporated by reference.

During the wetlay runs, it was found that the mat formed from thermoplastic materials is loose and without strength. Even extreme care was taken when handling, it still intended to break into parts, as shown in FIG. 10. It was also noticed that there is no binding between the large pieces of the thermoplastics, which prevents the formation a uniform and self-supporting mat. Therefore, a refining process was added prior to the actual wetlay mat formation. The refining process redistributes the pulp fibers in the medium and they behave as binders in the mat. The resulting mat is shown in FIG. 10 in comparison with a mat formed without refining. In addition to the usage in tray and panel forming via compression molding, the resulting coherent and self-supporting mat can also be a product by itself for applications such as filter, ground cover, erosion control mat, tree protection mat, weed mat etc.

A degradation problem with superabsorbent polymers was observed during growth media test. In the presence of rust (iron oxides) or any water soluble iron ions, superabsorbent polymers will lose its water absorbing capability. Iron can be a catalyst for degradation of superabsorbent polymers or simply crash them like calcium salts. As such, in one embodiment, it may be desirable to avoid iron in growth media as well as the container.

It is feasible to produce the proposed novel modular green roof product from recycled disposable diapers and it has many advantages over the products on the current market. The most unique features are super drought resistance and lightweight. Other associated features include reduced solid waste, better stormwater management, more energy saving, more beautiful landscaping, less pollution, etc.

The proposed manufacturing process, wet method separation and wetlay formation has been designed and initial trial runs with batch equipments have been finished. The results show that it is effective way to recycle disposable diapers with some modifications and continuous processes. This process and the product design allows 100% recycling of disposable diapers with different components converted to respective parts in a modular green roof product.

Vegetation development in this growth media was evaluated using a prototype green roof module. Within the limited study period, healthy plant growths are observed in growth media with 40-75% percent of recycled super absorbent polymers. Accelerated degradation studies under heat and UV irradiation showed relatively high TOC content in collected water sample. But it can be significantly lowered with simple treatment. Thermal and irradiation induced degradation may affect the life time of the growth media. A preliminary sanitation process was prepared and followed to clean dirty diapers. Common disinfection agent such as bleach at relatively low concentration performed satisfactory work in this study.

Example 1. Vegetation Establishment from Seeds in Growth Media

The growth media includes recovered SAP and light weight soil with several compositions. Lightweight soil is made of 22.74 vol % expanded clay (Miracle-Gro® prelate), 68.22 vol % peat moss (Miracle-Gro® peat moss) and 9.04 vol % water. The growth media compositions are: 100% SAP/0% soil, 75% SAP/25% soil, 50% SAP/50% soil, 25% SAP/75% soil and 0% SAP/100% soil by mass in wet state. The wet state means the maximum capacity of water holdup without free flowing water. These growth media were placed in containers of dimension with 20 cm×20 cm×4.5 cm. In each container, 400 Penkoted® grass seeds were planted in growth media at 5 mm deep. All these containers were placed in a simulated full sun environment at 24 hour per day. To maintain a healthy sprouting and growth of grass, extra water is provided during testing period. The extra water was provided so that no free water can be observed at any time. Because only a small amount of extra water was irrigated at around a week interval, the grasses in the growth media were exposed to a simulated drought condition.

The grass was sprouting and growing much less in the container with 100% SAP because of poor air permeability and poor root development. The sparsely sprouted grasses in this container died after two weeks. The grasses in the containers with 25% and 0% SAP initially sprout similarly with other two containers with 75% and 50% SAP. However, the growth of grasses in the former two containers eventually became slow and died in four weeks. In contrast, the two containers with 75% and 50% SAP were able to keep the grasses alive till 45 days and they can survive in another two weeks after watering. The total amount of extra water is about 3000 ml.

Example 2. Vegetation from Seeds in Growth Media with Nonwoven Cover

The growth media includes recovered SAP and light weight soil with several compositions. Lightweight soil is made of 22.74 vol % expanded clay (Miracle-Gro® prelate), 68.22 vol % peat moss (Miracle-Gro® peat moss) and 9.04 vol % water. The growth media compositions are: 100% SAP/0% soil, 75% SAP/25% soil, 50% SAP/50% soil, 25% SAP/75% soil and 0% SAP/100% soil by mass in wet state. The wet state means the maximum capacity of water holdup without free flowing water. These growth media were placed in containers of dimension with 20 cm×20 cm×4.5 cm. In each container, 400 Penkoted® grass seeds were planted in growth media at 5 mm deep. A nonwoven fabric is placed on top of the growth medium in each container. The nonwoven fabric is specially chosen so that the pore size is large enough for grass sprouts to grow through. All these containers were placed in a simulated full sun environment at 24 hour per day. To maintain a healthy sprouting and growth of grass, extra is provided during testing period. The extra water was provided so that no free water can be observed at any time. Because only a small amount of extra water was irrigated at around a week interval, the grasses in the growth media were exposed to a simulated drought condition.

The grass was sprouting and growing much less in the container with 100% SAP because of poor air permeability and poor root development. The sparsely sprouted grasses in this container died after two weeks. The grasses in the containers with 25% and 0% SAP initially sprout similarly with other two containers with 75% and 50% SAP. However, the growth of grasses in the former two containers eventually became slow and died five weeks after watering stopped. 45 days and they can survive in another two weeks after watering. However, the total extra water amount is only about 1800 ml. This result indicated that applying nonwoven cover on the top of growth media can dramatically decrease the water usage while still allow grass to survive a longer time during a drought condition.

Example 3. Use Dilute Sodium Chloride Solution as Separation Medium to Separate Diaper Components In a 1000 ml Flask, 15 gram of shredded diaper components were added firstly, then 1000 ml tap water was also added. The mixture was stirred and allowed for settle down for 15 minutes. After 15 minutes, however, it was hard to stir this mixture and there was no free water flowing in the flask. All the components in the flask all gel up because the SAP absorbs water and swell to much larger particles. However, by adding 5 gram sodium chloride into the flask, which make the total concentration of sodium chloride to 0.5% wt, the SAP particles shrunk to less than 50% of the size before sodium chloride is added. Hence, the mixture particles became easier to be stirred and free flowing. After further stirring and settle down, the majority of polyolefins such as polyethylenes and polypropylene float to the top of the flask, while SAP and sink down to the bottom of the flask. A separation can be made by removing the upper layer with most polyolefins and removing the lower layer with most SAP particles.

The efficiency of separation by a single settle down is not enough to remove SAP from thermoplastics. This is suggested by the water absorbing of the compression molded panels from the thermoplastics. So two more separations can be used to achieve higher purity of the polyolefins. The recovered thermoplastics is 10 gram and the recovered SAP is 250 gram in wet state, which is 5 gram after dried.

In a 5 gallon container, 8 liter tap water with 40 gram sodium chloride was used to separate 120 grams of shredded diaper components. After the lower layer where swelled SAP were removed, the solution was reused to separate the SAP in the thermoplastics that was recovered from the upper layer. This procedure was repeated for a total of three times. 80 grams of thermoplastics were recovered and 40 gram dried SAP was recovered. Finally 1000 L water was used to rinse the thermoplastics, which in turn can be reused for future separation.

Example 4. Use Dilute Potassium Chloride Solution as Separation Medium to Separate Diaper Component In a 1000 ml Flask, 15 gram of shredded diaper components were added firstly, then 1000 ml tap water was also added. The mixture was stirred and allowed for settle down for 15 minutes. After 15 minutes, however, it was hard to stir this mixture and there was no free water flowing in the flask. All the components in the flask all gel up because the SAP absorbs water and swell to much larger particles. However, by adding 5 gram potassium chloride into the flask, which make the total concentration of potassium chloride to 0.5% wt, the SAP particles shrunk to less than 50% of the size before potassium chloride is added. Hence, the mixture particles became easier to be stirred and free flowing. After further stirring and settle down, the majority of polyolefins such as polyethylenes and polypropylene float to the top of the flask, while SAP and sink down to the bottom of the flask. A separation can be made by removing the upper layer with most polyolefins and removing the lower layer with most SAP particles.

The efficiency of separation by a single settle down is not enough to remove SAP from thermoplastics. This is suggested by the water absorbing of the compression molded panels from the thermoplastics. So two more separations can be used to achieve higher purity of the polyolefins.

In a 5 gallon container, 8 liter tap water with 40 gram potassium chloride was used to separate 120 grams of shredded diaper components. After the lower layer where swelled SAP was removed, the solution was reused to separate the SAP in the thermoplastics that was recovered from the upper layer. This procedure was repeated for a total of three times. 80 grams of thermoplastics were recovered and 40 gram dried SAP was recovered. Finally 1000 L water was used to rinse the thermoplastics, which in turn can be reused for future separation.

Example 5. Use Calcium Chloride Dilute Solution as Separation Medium to Separate Diaper Components and SAP Recovery and Reinforcement In a 1000 ml Flask, 15 gram of shredded diaper components were added firstly, then 1000 ml tap water was also added. The mixture was stirred and allowed for settle down for 15 minutes. After 15 minutes, however, it was hard to stir this mixture and there was no free water flowing in the flask. All the components in the flask all gel up because the SAP absorbs water and swells into much larger particles. However, by adding 5 gram calcium chloride into the flask, which makes the total concentration of calcium chloride to 0.5% wt, the solution became cloudy and SAP agglomerated to small particles at the bottom. The volume of SAP particles shrunk to less than 200 ml. Hence, the mixture particles became easier to be stirred and free flowing. After further stirring and settle down, the majority of polyolefins such as polyethylenes and polyproplylene float to the top of the flask, while SAP and sink down to the bottom of the flask. A separation can be made by removing the upper layer with most polyolefins and removing the lower layer with most SAP particles. The thermoplastics collected after two separations by reusing the water solution are free of SAP and suitable for later processes.

The recovered SAP, unlike those recovered from sodium and potassium chloride solutions, is white particles with smaller particle sizes. However, the strength of the particles appears to be stronger.

However, if the concentration of calcium chloride is tripled, the SAP particles would shrink to minimal volume (less than 50 ml). And the separation efficiency is highly improved. The thermoplastics collected are free of SAP after just a single separation. However, the water absorption capacity of SAP is also lost and therefore the resulting SAP is useless in the current application where water absorption is critical. In this case, the collected SAP is referred to as "crashed SAP".

Example 6. Use Potassium Carbonate to Recover Calcium Crashed SAP

Crashed SAP small particles by calcium chloride solution in Example 8 were placed back into a 1 L flask with 500 ml water. 500 ml solution of potassium carbonate (3 grams) was added into the flask. The mixture was stirred allow settle down. After 4 hours, the crashed SAP small particles were observed to grow into larger particles. Eventually the total volume of SAP was recovered back to the 300 ml after overnight soaking. The surface water was filtered out and SAP small particles were rinsed by water for 3 times.

Example 7. Use Sodium Carbonate to Recover Calcium Crashed SAP

Crashed SAP small particles by calcium chloride solution in Example 8 were placed back into a 1 L flask with 500 ml water. 500 ml solutions of sodium carbonate (3 grams) were added into the flask. The mixture was stirred allow settle down. After 4 hours, the crashed SAP small particles were observed to grow into larger particles. Eventually the total volume of SAP was recovered back to the 300 ml after overnight soaking. The surface water was filtered out and SAP small particles were rinsed by water for 3 times.

Example 8. Compression Molding of Separated Diaper Components and Their Mechanical Properties The thermoplastics recovered from the upper layer of shredded diaper component were melt-pressed to make panels by using a hot press machine. Hot press machine was preheated to 400 F for about 20 mins. The thermoplastics strips and particles were placed between two stainless steel foil and covered by another two stainless steel plates, which are then placed in between two hot plates. Wait for 15 minutes after applying gentle pressure. Then use an approximate pressure of 5 ton/ft$^2$ and degassing by 3 times bump cycles to remove air bubbles in the plate. The films were then cooled down to room temperature in the air. Tensile tests indicated the strength is 8 MPa and the strain at break is less than 8%.

Both the tensile strength and elongation at break are considered as low for polyolefin materials and it will not be suitable for the intended applications. The fractured surfaces of these specimens were examined and it was concluded that the poor homogeneity and bonding of the thermoplastics strips and particles is the reason. The failure during a tensile test is usually due to the poor bonding between different materials in the specimen. So the materials must be homogenized to achieve better mechanical properties. A compounding process is incorporated to improve the mechanical properties as discussed in Example 11.

Example 9. Compounding and then Compression Molding of Separated Diaper Components and Their Mechanical Properties In a preheated (210° C.) mixing bowl of a Brabender Plasticorder blender (Model: 5650-M, Brabender), 200 grams of the recovered thermoplastics was added. Wait for 15 minutes for the plastics to soften or melt. The blender is then turned on to median speed for 20 minutes. Stop the blender and collect the blended materials. Use the same compression molding process described in Example 10 to press films and cut tensile test coupons, The tensile strength is found to be 11 MPa and the strain at break is found to be 14%.

Plastic compounding was carried in a sigma blender without inert gas protection. To avoid excessive oxidation to the materials, rather low mixing temperatures were used. Meanwhile, the mixing machine is batch mixer with limited shear stress capability. These factors caused limited mixing efficiency. An industrial version of mixer, twin-screw extruder may improve mixing efficiency and prevent oxidation with enclosed barrel and inert gas protection.

In one embodiment, a weed control and moisture conservation mat ("WCMC") is provided. In one embodiment, the mat is not intended to interfere with the root system like the agriculture applications of super absorbent polymers but rather the mat is used to hold large quantity of water above the root system. The water absorbed by SAP can seep into soil and maintain a high moisture atmosphere to slow down the moisture loss from soil.

The mat may be suitably used at any stage of the tree's growth, from seedling, to young tree, to a mature tree. In one embodiment, the mat may be used on a young tree or mature tree. In another embodiment, the mat may be used on a mature tree, and not on young tree or seedling.

Figure 13:
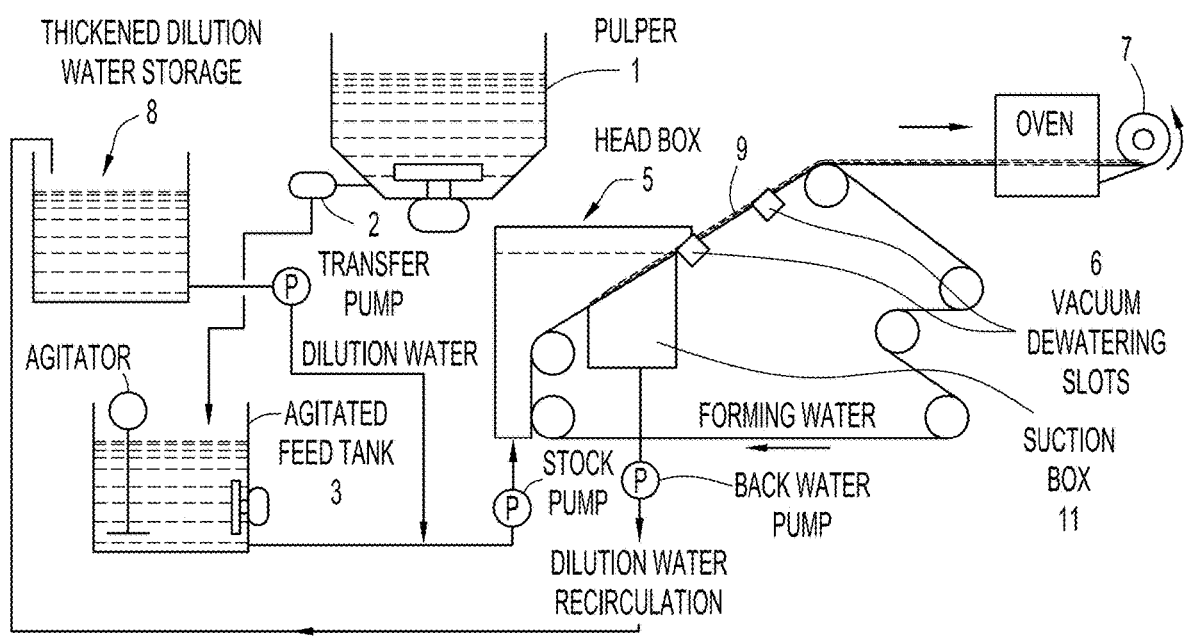
FIG. 13. Exhibit shows an example of process flow diagram for the wetlay process.

Wetlay is a modified paper-making process for nonwoven materials manufactured from fiber-like raw materials. In the wetlay process, as illustrated in FIG. 13, fibers are mechanically dispersed in an aqueous slurry solution (whitewater). The agitation of the mixture creates a slurry that is dewatered under vacuum as it is cast onto a moving, forming wire conveyor to form a continuous, non-woven, intermingled mat of the fibers. Whitewater filtrate is recycled and returned as dilution water. The resulting mat is subsequently fed into a convective through-air oven where it is dried and fused into a coherent, flexible, and highly porous mat. The resulting mat is then used either as the final product or as a feedstock for subsequent material processing. The result of this technology yields a competitive and cost-effective venue with minimal environmental impact to produce novel materials.

Figure 7:
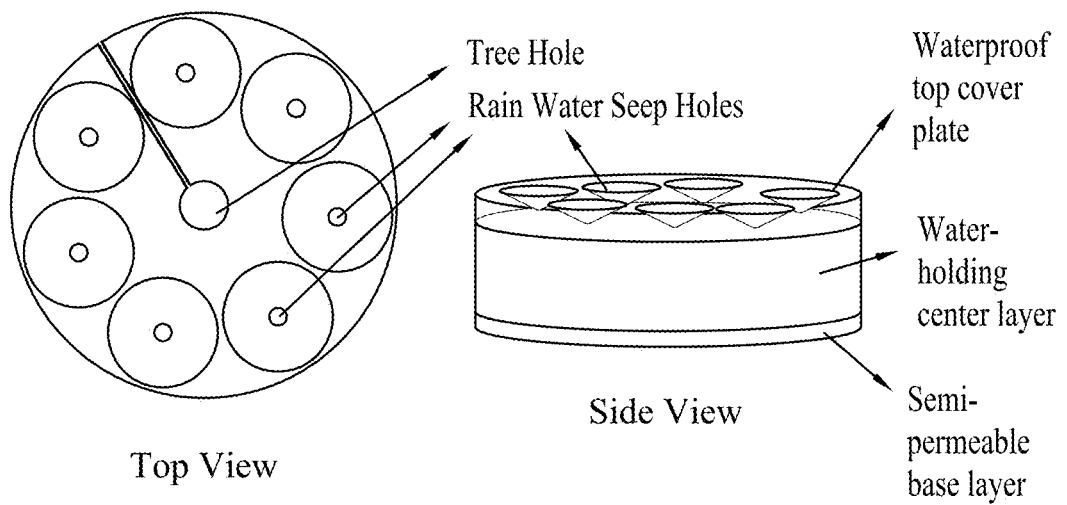
FIG. 7. One embodiment of a tree protection mat for weed control and moisture conservation.

Commercial weed mats suppress weed growth by eliminating their contact with air and light. Preservation of moisture is achieved by slow down evaporation. These two aspects can be utilized in the design of the proposed product with a top non-permeable layer. In one embodiment, an extra layer may be added that holds a large amount of water, water-holding layer. To slow down the releasing rate of water into soil, a semi-permeable layer can also be added. With the combination of a non-permeable top layer, a water-holding layer and a semi-permeable control layer, the mat can achieve the goals of weed control and moisture conservation. To allow rain water seep into the water-holding layer, seep holes or channels can be incorporated. FIG. 7 shows a model design of this weed control and moisture conservation (WCMC) mat.

In one embodiment, the basic components of the proposed WCMC mat including a waterproof top cover layer, a water-holding center layer and a semi-permeable base layer can be made from different parts of a disposable diaper. The waterproof top cover plate will be made of the polyolefin components from the diaper. High temperature compression molding will be needed to re-melt and solidify into non-permeable hard plates. The water-holding center layer will be made from a mixture of the superabsorbent polymers, cellulose, polyester, and polyolefin fibers. These components can be loosely bonded together to allow maximum amount of water absorbing capacity. Slow-releasing fertilizers may also be incorporated in this layer if desired. A semi-permeable base layer will be made of polyester nonwoven fibers. It will be welded onto the top cover plate to form a pocket sandwiching the water-holding layer. The base layer will also act as a protection layer during shipping and handling and as a moisture permeation regulation layer after installed.

Traditional efforts on recycling disposable diapers were not profitable because recycled materials with very high purity were targeted. The cost for obtaining high purity of recycled materials offsets all the possible profits in those developments. In contrast, high purity materials in the present application are not required. The only part that may need relatively high purity polymers is the top cover plate, where waterproof is required. As a result, the overall equipment requirement for separation is low. So will be the energy consumption and labor cost for this process. Furthermore, a rough separation can be achieved based only on the densities of the diaper components relative to water. They can be categorized as: polyolefins (low density), water swelled superabsorbent and cellulose, and polyesters (high density). They will float, suspend or sink in water resulting in a partial separation.

In one embodiment, features such as controlled-release fertilizer may be used in the center layer or green roof.

Figure 14:
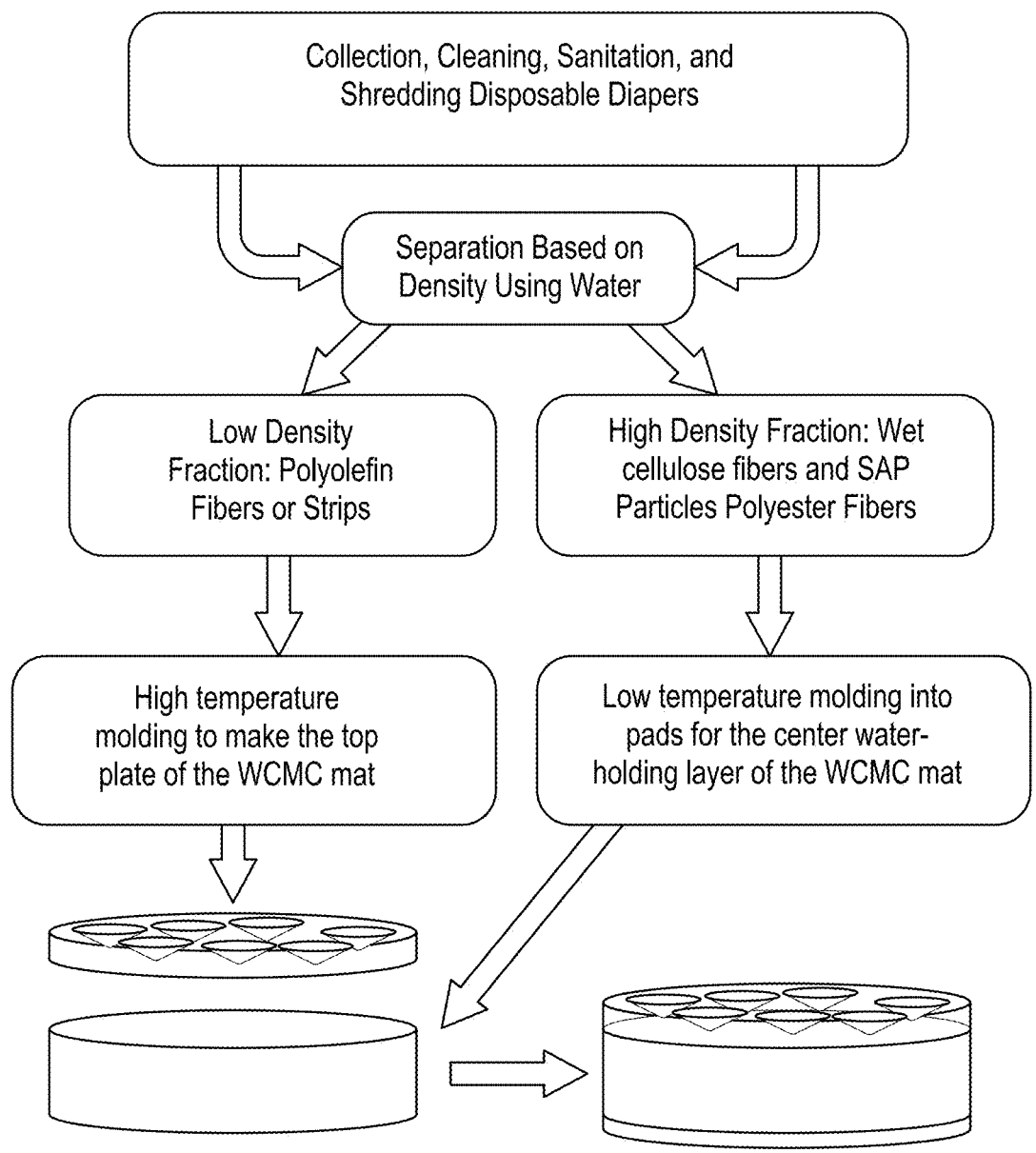
FIG. 14. Presents a flowchart of one embodiment of production process of weed control and moisture conservation mat from disposable diaper.

FIG. 14 shows a schematic flow chart of the one embodiment of the production process and design of WCMC mat. First step involves collection, cleaning and shredding the disposable diapers into short fibers and strips. Because disposable diapers are made by more than 10 different components, it is impossible to separate each individual component completely. Fortunately, they can be roughly and partially separated by their densities using water (specific gravity, SG=1) as the separation medium. The present inventors have found that they can be separated into two groups: heavier than water (SAP, polyester nonwoven and cellulose fibers) and lighter than water (majority is polyolefin materials). Their purities are poor and they are not suitable for other usages. Advantageously, the proposed application does not require high purity materials.

Figure 15:
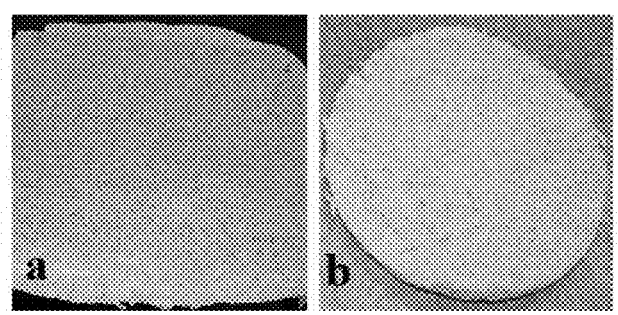
FIG. 15. Exhibit shows embodiments of panel and mat molded from recycled diaper materials.

After this partial separation of different diaper components, the polyolefin portion may be compression-molded into panels at high temperatures (above the melting temperatures of polyolefins). A sample is shown in FIG. 15a. These panels may be used as the top plate of the mat as the waterproof and support for the whole mat. The intermediate density portion may be compressed and dried to form pads for the center layer of the mat. The presence of cellulose fibers and small amount of polyester nonwovens helps this process and a self supporting mat can be made, FIG. 15b. The bottom layer of this design may be made from a porous and water permeable nonwoven or woven material. The porosity and the hydrophobicity of this layer can be tuned to control the permeability of water through this layer. After the individual layers are prepared, the WCMC mat can be assembled by compression molding or heat bonding around the edges.

It should be pointed out that the mechanical strength of the panels show in FIG. 15a is not very good due to poor mixing and adhesion of different components. But after further blending, the mechanical strength can be improved by at least 70%.

Figure 12:
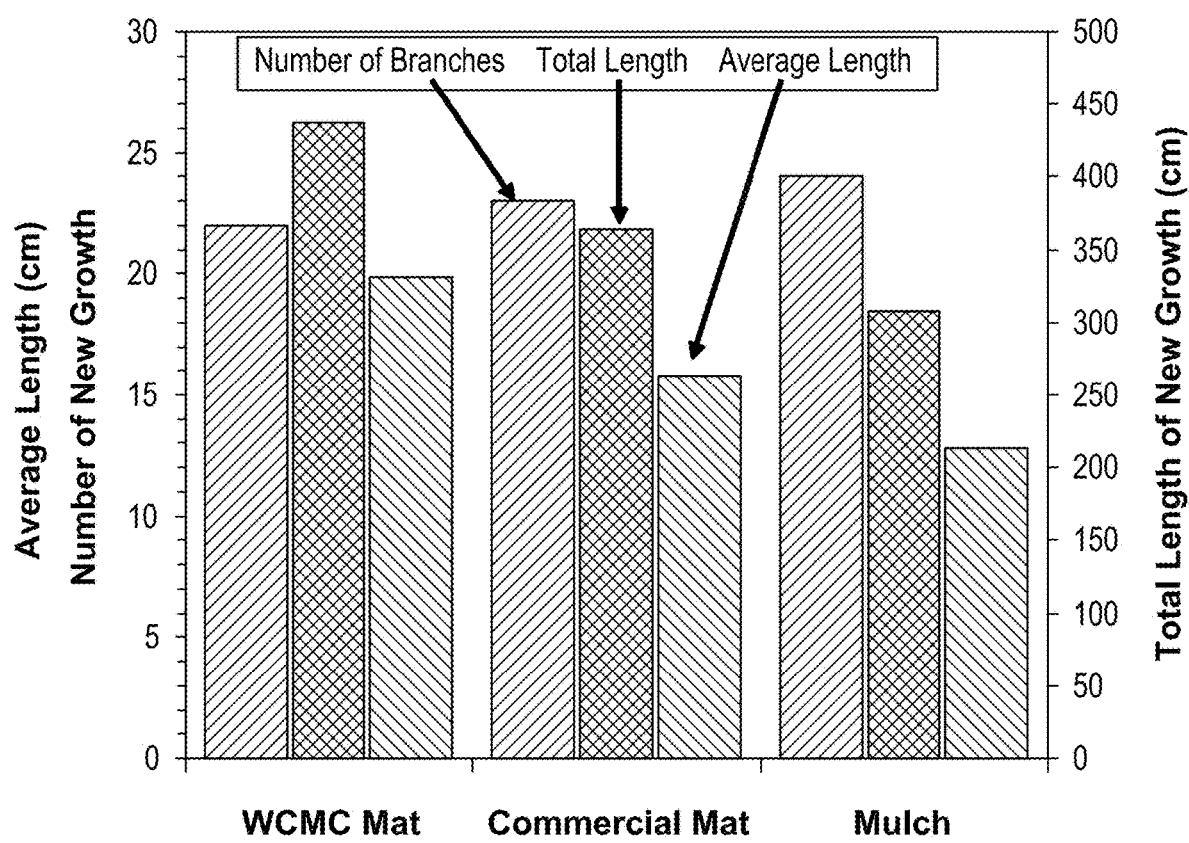
FIG. 12. Graphically shows the effect of WCMC mat on young tree growth after 5 months.

FIG. 12 shows a preliminary study on the effectiveness of the SAP on young tree protection after 5 months of usage. A simplified version of prototype WCMC, mulch only and a commercial mat was compared in this study. The average new growth of each branch, total length of new growth, total number of new branches were compared for three apple trees. It is clear that the WCMC mat is much better than the commercial weed mat and mulch only.

WCMC mat can offer fruit trees with sustained moisture around their root systems. If slow releasing fertilizer is incorporated, fertilizing and moisture can be regulated together at a steady rate based on trees' need. With the high water-holding capacity and weed suppressant function, WCMC mat will reduce the number of irrigation so to lower the costs on water, power, equipments, and labor. It will also reduce drought-related diseases and damages. With faster growth rate and higher survival rate, young fruit trees can yield better-quality fruits and sooner than others. In addition, farmers can improve the soil quality of wasteland and degraded soil areas by using the WCMC mat with regulated fertilizing and moisture control. Therefore, farmers can plant fruit trees in area that usually not suitable for them. Arid/semiarid areas can also be transformed and improved so that they are suitable for agriculture usage.

Not only can WCMC mat be used for trees directly related to food production, but this product can also be used to boost food production by increasing the total forest coverage of the surrounding areas of a farm. With the improved environment and better local climate near farms, food production can be indirectly increased. For an example, trees can be planted near farms as wind breakers to protect crops and reduce the loss of top soil. For another example, farms and orchards near a big forest do not need worry about pollinators, which nest in the neighborhood forest. The humidity and air temperature can also be regulated by the nearby forests.

As one way to restore the functions of forests, afforestation/reforestation is of great importance. Therefore, WCMC mat product will satisfy the public interest in that it can help tree protection, improve the survival rate and growth rate of young trees, reduce damages and death during droughts, allow afforestation in arid/semiarid regions, and enable reforestation on degraded soil and in wasteland areas. The product can help to reduce water and energy consumptions as well as lower labor and maintenance requirements on trees' after-planting cares. In summary, the WCMC mat can help to "protect and enhance the national's forest resources and environment".

One embodiment provides a light-weight, three-layer modular green roof tray. (1) The bottom layer as water-proof layer is made from recovered thermoplastic materials from recycling disposable diapers; (2) The center layer is a drought resistant growth medium containing superabsorbent polymers, and (3) The top layer is a porous nonwoven cover.

In one embodiment, the modular green roof tray contains a snap-fit locking mechanism. In one embodiment, the snap fit is a 3D locking mechanism. In one embodiment, the snap fit includes an adhesive placed on the snap tongue portion. In one embodiment, the interlocked modular uses weight to hold on top of roof. In one embodiment, weight is not used to hold on top of roof.

In one embodiment, the cover of green roof tray may be made by low density and large pore-sized nonwoven mat. In one embodiment, this cover performs as an enclosure of growth medium during the shipping and installation, allows plants to grow through the pores, prolongs water retention time of growth medium, and prevents erosion.

In one embodiment, the non-woven mat cover has 70% longer water retention time for growth medium than that without the cover.

In one embodiment, the growth medium composition of green roof tray contains 90-20% SAP optimum at 65%.

In one embodiment, the SAP act as drought resistant component.

In one embodiment, the SAP is recycled and recovered from disposable diapers.

In one embodiment, when the growth medium composition is used as potting soil for indoor house plants such as Dwarf Umbrella tree (*Schefflera arboricola*) and Kentia palm (*Howey forsteriana*), watering frequency can be reduced down to once every 12 weeks.

In one embodiment, the growth medium composition is also applicable to one or more of non-modular green roof design, indoor house plants, other horticulture plants.

In one embodiment, the SAP may be recovered from disposable diaper as follows:

i. Dilute calcium chloride solution. Ratio of $CaCl_2$ to dry SAP is 3:10. This not only can efficiently separate SAP from the rest of the pulp, but also improves the gel strength. The mechanism for this gel strength enhancement is that calcium polyacrylate behaves as a physical crosslinker ii. In conventional systems, the SAP was not recovered. A much higher concentration of calcium solution was used that results SAP were all crashed out. This work is to use dilute calcium solution and control the ratio of calcium and SAP.

iii. Recovering crashed SAP due to high calcium concentration can be done by applying solutions of potassium or sodium carbonate. Calcium then reacts with carbonate to form calcium carbonate and release the polyacrylate to reform sodium or potassium polyacrylate.

In one embodiment, the plastics or thermoplastics may be recovered from diaper materials using wet method.

In one embodiment, a compounding process may be applied to the plastics recovered from diaper.

In one embodiment, the tree protection mat has a water absorption capability such that it can slowly release water into soil.

One embodiment relates to a process for recycling soiled disposable diapers, comprising:
  contacting a plurality of soiled disposable diapers with at least one bleaching agent to sanitize the diapers, to form a mixture comprising sanitized diaper components;
  shredding the sanitized diaper components, to form a shredded mixture comprising thermoplastics and superabsorbent polymer particles;
  contacting the shredded mixture with a first salt solution to increase the density of the superabsorbent polymer particles and form a density-separated mixture having an upper layer comprising thermoplastics and a lower layer comprising superabsorbent polymer particles and wastewater;
  separating the upper layer from the lower layer, to obtain separated thermoplastics and separated superabsorbent polymer particles;
  compounding the separated thermoplastics in an extruder to form a thermoplastic polymer blend; and
  separating the separated superabsorbent polymer particles from the wastewater.

In one embodiment, the thermoplastics comprise one or more polyolefins.

In one embodiment, the thermoplastics are one or more polymers selected from the group consisting of polyethylene, polypropylene, copolymer of ethylene and other alkene, HDPE, LDPE, copolymer of two or more thereof, and a combination of two or more thereof.

In one embodiment, the thermoplastics further comprise one or more selected from the group consisting of polyester, polyacrylic, cellulose, elastomer, nylon fiber, polyethylene fiber, polypropylene fiber, and a combination of two or more thereof.

In one embodiment, the superabsorbent polymer particles comprise polyacrylic acid polymer, polyacrylate polymer, starch-grafted polymer, polyacrylamide, ethylene maleic anhydride polymer, carboxymethylcellulose, polyvinyl alcohol, polyethylene oxide, starch grafted copolymer of polyacrylonitrile, Group IA salts of polyacrylic acids, copolymer of two or more thereof, or a combination of two or more thereof.

In one embodiment, the superabsorbent polymer particles are crosslinked, linear, copolymeric, or a combination of two or more thereof.

In one embodiment, the bleaching agent is selected from the group consisting of sodium hypochlorite, potassium hypochlorite, chlorine, ozone, oxygen, calcium hypochlorite, hydrogen peroxide, chlorine dioxide, and a combination of two or more thereof.

In one embodiment, the bleaching agent is selected from the group consisting of sodium hypochlorite, potassium hypochlorite, and a combination thereof.

In one embodiment, the first salt solution is an aqueous solution of at least one Group IA, IIA, IIIA, or VIIIA metal salt, or a combination of two or more thereof.

In one embodiment, the first salt solution is an aqueous solution of at least one Group IIA or IIIA metal salt, or a combination thereof.

In one embodiment, the first salt solution is an aqueous solution of at least one Group IIA metal salt, or a combination thereof.

In one embodiment, the first salt solution is an aqueous solution of sodium chloride, potassium chloride, calcium chloride, sodium carbonate, potassium carbonate, calcium carbonate, sodium hydrogen carbonate, potassium hydrogen carbonate, sodium nitrate, potassium nitrate, calcium nitrate, sodium hypochlorite, potassium hypochlorite, calcium hypochlorite, aluminum salt, boron salt, iron salt, or a combination of two or more thereof.

In one embodiment, the first salt solution is an aqueous solution of calcium salt.

In one embodiment, the separated superabsorbent polymer particles are contacted with a second salt solution to decrease the density of the separated superabsorbent polymer particles, to form a mixture comprising decreased density superabsorbent polymer particles and a second wastewater.

In one embodiment, the decreased density superabsorbent polymer particles are separated from the second wastewater.

In one embodiment, the second salt solution is an aqueous solution of at least one Group IA, IIA, or IIIA metal salt, or a combination of two or more thereof.

In one embodiment, the second salt solution is an aqueous solution of at least one Group IA or IIA metal salt, or a combination thereof.

In one embodiment, the second salt solution is an aqueous solution of at least one Group IA metal salt, or a combination thereof.

In one embodiment, the second salt solution is an aqueous solution of sodium chloride, potassium chloride, sodium carbonate, potassium carbonate, sodium sulfate, potassium sulfate, sodium nitrate, potassium nitrate, or a combination of two or more thereof.

In one embodiment, the second salt solution is an aqueous solution of a sodium salt, potassium salt, or a combination thereof.

In one embodiment, the upper and lower layers are separated by screening, filtering, decanting, centrifuging, hydrocycloning, moving web, or a combination of two or more thereof.

In one embodiment, the separated superabsorbent polymer particles are dried.

In one embodiment, the separated superabsorbent polymer particles are contacted with soil, earth, mulch, peat moss, biomass, compost, topsoil, sand, organic plant growth material, nitrogen-containing fertilizer, phosphorus-containing fertilizer, lime, herbicide, potting soil, growth medium, fertilizer, or a combination of two or more thereof, to form a plant growth medium.

One embodiment provides a plant growth medium, produced by the process described herein.

One embodiment provides a process for growing plants, comprising contacting the plant growth medium with a plant or seed.

In one embodiment, the compounding is carried out in a batch process, a continuous process, or a combination thereof.

In one embodiment, the extruder is a single screw or multi screw extruder, or a combination thereof.

In one embodiment, one or more of molding, extruding, thermoforming, or pelletizing the thermoplastic polymer blend, may be used to form a plastic article.

In one embodiment, molding is injection molding, compression molding, rotational molding, or a combination of two or more thereof.

In one embodiment, the thermoplastic polymer blend is contacted with epoxy; adhesive; virgin or recycled resin of one or more of polyethylene, polypropylene, polyester, or other thermoplastic; fiber, reinforcement fiber, glass fiber, carbon fiber, aramid fiber, wood fiber, plant fiber, cellulose, filler, clay, nanoclay, carbon black, carbon nanotube, glass bead, silica, titanium dioxide, calcium carbonate, fire retardant, pigment, antioxidant, fragrance, or a combination of two or more thereof.

One embodiment provides a plastic article, produced by the process described herein.

One embodiment provides a modular green roof tray, comprising:
a waterproof bottom layer made from a thermoplastic material;
a center layer disposed over the bottom layer and comprising a drought resistant growth medium containing superabsorbent polymer particles; and
a porous nonwoven top cover disposed over the center layer.

In one embodiment, side walls made from the thermoplastic material are provided, said walls surrounding side portions of the center layer.

In one embodiment, one or more of the side walls further comprise a snap-fit locking mechanism.

In one embodiment, the snap-fit locking mechanism are capable of snap-fitting and locking to one or more side walls of an adjacent modular green roof tray.

In one embodiment, the porous nonwoven material is a low density and large pore-sized nonwoven mat.

In one embodiment, the growth medium comprises 90-20% by weight of the superabsorbent polymer particles.

In one embodiment, the growth medium comprises about 65% by weight of the superabsorbent polymer particles.

FIG. 12 graphically shows the effect of one embodiment of the tree protection mat on the growth of three newly planted apple trees after 5 months. In this figure a treep protection mat, hardwood mulch and a commercial weed mat made of recycled rubber strips that without superabsorbent polymer particles were compared. The average new growth of each branch, total length of new growth, and total number of new branches were compared. It is clear that the tree protection mat is much better than the commercial weed mat and hardwood mulch.

One embodiment provides a tree protection mat, comprising:
a top cover plate, comprising a waterproof material having holes therein to permit water to flow therethrough;
a center layer disposed beneath the cover plate and comprising superabsorbent polymer particles; and
a semipermeable bottom layer disposed beneath the center layer.

One embodiment provides a tree protection mat, comprising:
a top cover plate;

a center layer disposed beneath the cover plate and comprising superabsorbent polymer particles; and a semipermeable bottom layer disposed beneath the center layer;

wherein the top cover plate reduces or prevents evaporative water loss from the center layer.

The choice of material for the top cover plate is not particularly limited, so long as it reduces or prevents evaporative water loss from the center layer. The top cover plate material may be made of thermoplastic such as polyethylene or other plastic film or laminate; may be woven or nonwoven; it may be waterproof or semipermeable to water; it may be unperforated or perforated with holes or small funnels, for example of the type used in VISPORE™ Tree Mat materials; or any combination thereof. In one embodiment, the top cover plate material includes one or more UV resistant additives, to resist against sun damage.

The top cover plate may be waterproof and prevent evaporative water loss from the center layer. It may also be semipermeable to water, and allow water in the form of moisture, precipitation, or watering, to flow through to the center layer; or it may include an opening, such as a hose fitting, to allow connection to a water hose, and thereby water and optionally growth media such as fertilizer can be pumped through the fitting and hydrate the center layer; or any combination thereof.

So long as it allows water to seep down into the ground from the center layer, the choice of material for the semipermeable bottom layer is not particularly limiting. For example, it may be made of woven or nonwoven fabric, semipermeable material, natural or synthetic fiber, rayon, nylon, polyester, polyethylene, polypropylene, cotton, nylon, acrylic, or the like, or any combination thereof.

The top cover plate, center layer, and semipermeable bottom layer may be sandwiched together, in the order prescribed herein, and optionally sealed at the perimeter edge by sewing, gluing, heat sealing, or the like. Alternatively, it may include a sidewall, which extends around the perimeter, which sidewall may be waterproof or semipermeable to water. The sidewall may be connected to the top cover plate, center layer, and semipermeable layer as appropriate. In either case, the mat may include an access slit and a hole in the center, such as shown in FIG. 7, to allow placement around the trunk or stem of the tree, shrub, bush, sapling, or other plant. The sides of the access slit may include ties, snaps, Velcro, zipper, or similar methods of connecting the two sides of the slit to one another. The mat may lay flat or it may have a built-in shape such as a cone or rounded shape, for example, to accommodate the ground around the subject plant or to accommodate the shape of the plant itself.

In one embodiment, the top cover plate reduces evaporative water loss from the center layer. In another embodiment, the top cover plate prevents evaporative water loss from the center layer.

In one embodiment, dry SAP refers to SAP at standard temperature and pressure. In one embodiment, dry SAP contains about 10% by weight of water.

This application is based on and claims priority to U.S. Provisional Application Ser. No. 61/538,565, filed Sep. 23, 2011, the entire contents of which are hereby incorporated by reference, the same as if set forth at length.

The invention claimed is:

1. A tree or plant protection mat, comprising:
a semipermeable top cover plate comprising woven polypropylene fabric, woven polyethylene fabric, or a combination thereof;
a center layer disposed beneath the cover plate and comprising superabsorbent polymer particles selected from the group consisting of polyacrylic acid polymer, polyacrylate polymer, starch-grafted polymer, polyacrylamide, ethylene maleic anhydride polymer, carboxymethylcellulose, polyvinyl alcohol, polyethylene oxide, starch grafted copolymer of polyacrylonitrile, Group IA salts of polyacrylic acids, copolymer of two or more thereof, and any combination thereof; and
a semipermeable bottom layer disposed beneath the center layer;
wherein the top cover plate and semipermeable bottom layer are sealed together at their perimeter edges, by sewing, gluing, heat sealing, or any combination thereof, to sandwich the center layer between the top cover plate and semipermeable bottom layer;
wherein the top cover plate is semipermeable to water, and allows water in the form of moisture, precipitation or watering to flow through to the center layer, and reduces evaporative water loss from the center layer; and
wherein the semipermeable bottom layer permits water to seep out from the center layer onto the ground, when the mat is placed on the ground near a trunk or stem of the tree or plant;
wherein the mat does not have a hose fitting or other opening for connecting to a water hose.

2. The mat of claim 1, wherein the superabsorbent polymer particles are dry.

3. The mat of claim 1, wherein the center layer further comprises one or more cellulose fibers, polyester fibers, and polyolefin fibers, controlled-release fertilizer, or any combination thereof.

4. The mat of claim 1, wherein the semipermeable bottom layer comprises woven or nonwoven fabric, natural or synthetic fiber, rayon, nylon, polyester, polyethylene, polypropylene, cotton, acrylic, or any combination thereof.

5. The mat of claim 1, wherein the semipermeable bottom layer comprises nonwoven polyethylene fabric, nonwoven polypropylene fabric, or a combination thereof.

6. The mat of claim 1, further comprising a sidewall extending around a perimeter of the mat, wherein the top cover plate and semipermeable bottom layer are sealed at their perimeter edges to the sidewall.

7. The mat of claim 1, further comprising a hole, and an access slit, through the top cover plate, center layer, and bottom layer, for a tree or plant.

8. A method for growing a tree or plant, comprising placing the mat of claim 1 near a trunk or stem of the tree or plant.

9. A method for making the mat of claim 1, comprising sandwiching the center layer between the top cover plate and the semipermeable bottom layer, optionally with the side layer, to provide the mat.

* * * * *